(12) United States Patent
Leinen et al.

(10) Patent No.: US 6,506,366 B1
(45) Date of Patent: Jan. 14, 2003

(54) LIQUID TOOTH CLEANING GEL

(75) Inventors: Hans-Theo Leinen, Duesseldorf (DE); Dorothea Gregori, Neuss (DE); Miracle Pujol, Teia (ES); Maria Rosa Carbó, Barcelona (ES)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/806,433

(22) PCT Filed: Sep. 22, 1999

(86) PCT No.: PCT/EP99/07043

§ 371 (c)(1),
(2), (4) Date: Jul. 19, 2001

(87) PCT Pub. No.: WO00/19970

PCT Pub. Date: Apr. 13, 2000

(30) Foreign Application Priority Data

Oct. 1, 1998 (DE) .......................................... 198 45 247

(51) Int. Cl.[7] ................................................. A61K 7/16
(52) U.S. Cl. ...................................................... 424/49
(58) Field of Search .................. 404/49–88; 424/49–88

(56) References Cited

U.S. PATENT DOCUMENTS

| | | | | |
|---|---|---|---|---|
| 3,538,230 A | | 11/1970 | Pader et al. ................... | 424/50 |
| 3,767,791 A | * | 10/1973 | Cordon et al. ................ | 424/49 |
| 3,803,301 A | * | 4/1974 | Cordon et al. ................ | 424/49 |
| 3,934,000 A | * | 1/1976 | Barth .......................... | 424/49 |
| 3,935,306 A | * | 1/1976 | Roberts et al. ................ | 424/49 |
| 4,089,943 A | * | 5/1978 | Roberts et al. ................ | 424/49 |
| 4,108,978 A | | 8/1978 | Mazanobile et al. ........... | 424/49 |
| 4,153,680 A | | 5/1979 | Seybert ....................... | 424/49 |
| 4,294,894 A | * | 10/1981 | Velluci ........................ | 424/49 |
| 4,456,585 A | * | 6/1984 | Hayes et al. .................. | 424/49 |
| 4,618,488 A | | 10/1986 | Maeyama et al. ............. | 424/49 |
| 4,857,289 A | | 8/1989 | Nauroth et al. .............. | 423/339 |
| 5,074,917 A | * | 12/1991 | Persello ....................... | 106/436 |
| 5,178,869 A | * | 1/1993 | Ebine et al. ................. | 424/401 |
| 5,252,313 A | * | 10/1993 | Collins et al. ................ | 424/49 |
| 5,582,816 A | * | 12/1996 | Mandanas et al. ............. | 424/49 |
| 5,628,985 A | * | 5/1997 | Stiller et al. .................. | 424/49 |
| 5,695,746 A | * | 12/1997 | Garlick et al. ................ | 424/49 |
| 6,074,629 A | * | 6/2000 | Kostinko et al. ............. | 424/49 |
| 6,143,280 A | * | 11/2000 | Pike et al. .................... | 424/49 |

FOREIGN PATENT DOCUMENTS

| | | | |
|---|---|---|---|
| CA | 1049228 | | 2/1979 |
| CA | 2140370 | | 1/1994 |
| DE | 22 50 078 | | 4/1973 |
| DE | 25 22 486 | | 11/1975 |
| DE | 31 14 493 | | 10/1982 |
| DE | 35 27 280 | | 2/1986 |
| DE | 195 22 750 | | 1/1997 |
| FR | 2 183 228 | | 12/1973 |
| WO | 94/01080 | * | 1/1994 |
| WO | WO95/22958 | | 8/1995 |
| WO | 00/03676 | * | 1/2000 |
| WO | 00/19970 | * | 4/2000 |

* cited by examiner

Primary Examiner—Shep K. Rose
(74) Attorney, Agent, or Firm—Stephen D. Harper

(57) ABSTRACT

The present invention relates to a liquid transparent tooth cleaning composition containing silica polishing components, humectant and water. The humectant includes sorbitol (a), glycerol (b) and polyethylene glycol (c) in a weight ratio of (a) to (b) to (c) of 10:(7 to 8):(0.5 to 1.5).

12 Claims, No Drawings

LIQUID TOOTH CLEANING GEL

CROSS REFERENCE TO RELATED APPLICATIONS

This application is a national stage application under 35 U.S.C. § 371 of international application PCT/EP99/07043 filed on Sep. 22, 1999, the international application not being published in English. This application also claims priority under 35 U.S.C. § 119 to DE 198 45 247.0 filed on Oct. 1, 1998.

This invention relates to liquid tooth cleaning preparations containing polishes, humectants and water which are substantially transparent or clear and which show favorable Theological behavior for dispensing from small flexible plastic bottles.

BACKGROUND OF THE INVENTION

Liquid tooth cleaning preparations which can be dispensed under light pressure from small flexible plastic bottles are already known, for example from WO 94/01080 A1. These products are white or opaque in appearance. In order to formulate transparent or clear products, the liquid carrier of water, humectants and optionally dissolved ingredients must have a refractive index similar to the polish. WO 95/22958, for example, describes a transparent formulation which contains more than 50% by weight of sorbitol. However, the transparency of these liquid tooth gels does not show satisfactory stability to low temperatures. WO 94/01080 A1 also describes transparent liquid tooth cleaning preparations which contain ca. 21% by weight of sorbitol, 30% by weight of glycerol and 5% by weight of ethanol. These known liquid tooth cleaning preparations have very low viscosities of well below 10,000 mPa·s (25° C.).

The problem addressed by the present invention was to provide a liquid tooth cleaning preparation which, although remaining transparent at low temperatures, would not be too liquid and, when applied to a toothbrush, would not sink too quickly or too deeply into the bristles.

The problem stated above has been solved by the use of a specific humectant mixture.

DETAILED DESCRIPTION OF THE INVENTION

The present invention relates to a liquid transparent tooth cleaning preparation containing
  10 to 15% by weight of silica polishing components,
  55 to 70% by weight of humectants (a+b+c),
  15 to 30% by weight of water and
  2 to 10% by weight of other toothpaste ingredients,
  characterized in that a mixture of sorbitol (a), glycerol (b) and polyethylene glycol (c) in a ratio by weight of (a) to (b) to (c) of 10:(7–8):(0.5–1.5) is present as the humectant.

Liquid in the context of the present invention means a viscosity of ca. 10,000 to 100,000 mPa·s (as measured at 20° C. with a Brookfield RVF rotational viscosimeter, spindle ¾ at 4 r.p.m. corresponding to a shear rate D of 4 s$^{-1}$) which provides for easy dispensing from a small flexible bottle and ensures that the gel sinks slowly into the bristles of the toothbrush.

Transparency should be at least so high that text with a letter height of ca. 4 mm and a letter width of 3 mm is still easy to read through a ca. 1 cm thick layer of the tooth gel (for example in a clear glass cell with an edge length of 1×1×4 cm).

Suitable silica polishing components are any silica gels, silica hydrogels and precipitated silicas known as polishes. Silica gels are obtained by reacting sodium silicate solutions with strong aqueous mineral acids to form a hydrosol, ageing to form the hydrogel, washing and drying. If drying is carried out under moderate conditions to a water content of 15 to 35% by weight, the so-called silica hydrogels known, for example, from U.S. Pat. No. 4,153,680 are obtained. Drying to water contents below 15% by weight results in irreversible shrinkage of the previously loose structure of the hydrogel to the dense structure of the so-called xerogel. Silica xerogels are described, for example, in U.S. Pat. No. 3,538,230.

A second particularly suitable group of silica polishing agents are the precipitated silicas. Precipitated silicas are obtained by precipitation of silica from dilute alkali metal silicate solutions by addition of strong acids under conditions which preclude aggregation to the sol and gel. Suitable processes for the production of precipitated silicas are described, for example, in DE-OS 25 22 486 and in DE-OS 31 14 493. A particularly suitable precipitated silica is that produced in accordance with DE-OS 31 14 493 which has a BET surface of 15 to 110 m$^2$/g, a particle size of 0.5 to 20 μm (at least 80% by weight of the primary particles should be below 5 μm in size) and a viscosity in the form of a 30% glycerol/water (1:1) dispersion of 30 to 60 Pa·s (20° C.) and which is used in a quantity of 10 to 20% by weight, based on the toothpaste. In addition, particularly suitable precipitated silicas of this type have rounded corners and edges and are commercially obtainable under the name of Sident®12 DS (DEGUSSA).

Other precipitated silicas of this type are Sident 8 (DEGUSSA) and Sorbosil AC 39 (Crosfield Chemicals). These silicas are distinguished by a weaker thickening effect and a slightly larger mean particle size of 8 to 14 μm for a specific BET surface of 40 to 75 m$^2$/g and are particularly suitable for liquid tooth gels according to the present invention.

Other polishes, particularly those with a refractive index differing from 1.45 μm by more than 0.1, are preferably not present at all or are present at most in quantities of less than 2% by weight.

Of crucial importance to the rheology and transparency of the liquid tooth cleaning gels according to the invention is the composition of the liquid carrier phase of water and humectants. The total quantity of 55 to 70% by weight of humectants is composed of sorbitol (a), glycerol (b) and polyethylene glycol (c) in a relatively narrow quantity ratio of (a) to (b) to (c) of 10:(7–8):(0.5–1.5). Accordingly, for a preferred sorbitol content of 30 to 35% by weight, the glycerol content is 21 to 28% by weight and the polyethylene glycol content 1.5 to 5.25% by weight.

Water (d) and humectant (a+b+c) are preferably present in a ratio by weight of (d):(a+b+c)=1:(2–3). For a preferred content of 55 to 65% by weight of humectants, the water content is 20 to 25% by weight. The water content is the sum of the water introduced by raw materials such as, for example, 70% sorbitol or 86% glycerol and the water separately added. The quantities of sorbitol and glycerol mentioned are based on water-free active substance.

In addition to the compulsory components mentioned, the tooth cleaning gels according to the invention may contain other toothpaste ingredients which, in type and quantity, do not adversely affect transparency. Such ingredients are, for example, binders, surfactants, flavors, substances active against diseases of the teeth and gums, for example fluorine compounds, scale inhibitors, antibacterial agents (for example biguanides, Triclosan), vitamins, panthenol and other active substances.

Finally, the transparent tooth cleaning gels according to the invention are also eminently suitable for conversion into attractive-looking products by soluble dyes and/or colored pigments. Particularly suitable colored pigment particles are the colored silica particles commercially available, for example, under the names of Sorbosil BFG 51, BFG 52 and BFG 53 and Sorbosil SD 2352. Mixtures of differently colored pigment particles may also be used. These silica gel particles colored, for example, bright orange, red or blue may be present in the tooth cleaning gels according to the invention in quantities of 0.1 to 1.0% by weight.

Suitable binders are, for example, natural and/or synthetic water-soluble polymers, such as alginates, carrageenates, tragacanth, starch and starch ethers, cellulose ethers such as, for example, carboxymethyl cellulose (Na salt), hydroxyethyl cellulose, methyl hydroxypropyl cellulose, guar, acacia gum, agar agar, xanthan gum, succinoglycan gum, locust bean gum, pectins, water-soluble carboxyvinyl polymers (for example Carbopol® types), polyvinyl alcohol, polyvinyl pyrrolidone, polyethylene glycols, more particularly those with molecular weights of 1,500 to 1,000,000.

Particularly suitable binders are xanthan gum, carboxymethyl cellulose, polyvinyl pyrrolidone and mixtures of these water-soluble polymers which may be present in a quantity of up to 0.5% by weight.

Suitable surfactants are, for example, sodium alkyl sulfates containing 12 to 18 carbon atoms in the alkyl group. These compounds also have an enzyme-inhibiting effect on the bacterial metabolism of tartar. Other suitable surfactants are alkali metal salts, preferably sodium salts of alkyl polyglycol ether sulfate containing 12 to 16 carbon atoms in the linear alkyl group and 2 to 6 glycol ether groups in the molecule, of linear alkane ($C_{12-18}$) sulfonate, of sulfosuccinic acid monoalkyl ($C_{12-18}$) esters, of sulfated fatty acid monoglycerides, sulfated fatty acid alkanolamides, sulfoacetic acid alkyl ($C_{12-16}$) esters, acyl sarcosines, acyl taurides and acyl isethionates containing 8 to 18 carbon atoms in the acyl group. Zwitterionic, ampholytic and nonionic surfactants, for example ethoxylates of fatty acid mono- and diglycerides, of fatty acid sorbitan esters and alkyl (oligo) glucosides, are also suitable.

Sodium lauryl sulfate and a mixture of sodium lauryl sulfate and Cocoamidopropyl Betaine are particularly suitable.

Flavors and sweeteners are normally used for flavoring. Suitable flavors are, for example, peppermint oil, spearmint oil, eucalyptus oil, aniseed oil, fennel oil, caraway oil, methyl acetate, cinnamaldehyde, anethol, vanillin, thymol and other natural or nature-identical essential oils or even synthetic flavors.

Suitable sweeteners are, for example, saccharin sodium, sodium cyclamate, sucrose, lactose, maltose or fructose.

Other typical toothpaste ingredients are, for example, preservatives and antimicrobial agents, for example p-hydroxybenzoic acid methyl, ethyl or propyl ester, sodium sorbate, sodium benzoate, bromochlorophene, Triclosan, hexetidine, phenyl salicylate, biguanides, for example chlorhexidine, and peroxides;

fluorine compounds such as, for example, Na fluoride, zinc fluoride, Na monofluorophosphate, amine fluoride, etc.

buffering agents, for example primary, secondary or tertiary alkali metal phosphates, citric acid/Na citrate, wound-healing and anti-inflammatory agents such as, for example, urea, allantoin, panthenol, alkali metal thiocyanates, camomile-based active principles (azulene) and acetylsalicylic acid derivatives;

vitamins such as, for example, retinol, tocopherol or ascorbic acid and mineral salts such as, for example, manganese, zinc or magnesium salts.

All these optional toothpaste ingredients together are present in the tooth gels according to the invention in a quantity of about 2 to 10% by weight.

The following Examples are intended to illustrate the invention.

EXAMPLES

Liquid tooth cleaning gels with the following composition were prepared:

| | 1 | 2 | 3 | 4 | 5 | 6 |
|---|---|---|---|---|---|---|
| Sident 12 SPLS | 12 | 12 | 12 | 12 | 12 | 12 |
| Sipernat 320 DS | — | — | — | — | 0.5 | — |
| Sorbosil BFG 51 | 0.1 | 0.1 | 0.1 | 0.1 | 0.1 | 0.1 |
| Sorbitol | 33.6 | 33.6 | 33.6 | 33.6 | 33.6 | 33.6 |
| Glycerol | 24.3 | 24.3 | 23.9 | 24.3 | 23.9 | 23.9 |
| Polyethylene glycol 400 | 3.8 | 3.8 | 3.8 | 3.8 | 3.8 | 3.8 |
| Keltrol F | — | 0.15 | — | — | — | 0.2 |
| Blanose 9-M-31-XF | — | — | — | — | 0.2 | — |
| Blanose 12-M-31-P | — | — | 0.25 | 0.25 | — | — |
| Luviskol K30 | — | 0.01 | — | — | 0.02 | — |
| Texapon K12 | 0.5 | 0.5 | 0.5 | 0.5 | 0.5 | 0.5 |
| Tego Betain F50 | 0.72 | 0.72 | 0.72 | 0.72 | 0.72 | 0.72 |
| Cremophor RH60 | — | — | — | — | — | — |
| Tagat S | — | — | — | — | — | — |
| Flavor | 0.8 | 0.8 | 0.8 | 0.8 | 0.8 | 0.8 |
| Na saccharin | 0.25 | 0.25 | 0.25 | 0.25 | 0.25 | 0.25 |
| Panthenol | — | — | — | — | — | — |
| Retinol palmitate | — | — | — | — | — | — |
| $Na_2PO_3F$ | 1.1 | 1.1 | 1.1 | 1.1 | 1.1 | 1.1 |
| Water | to 100 | to 100 | to 100 | to 100 | to 100 | to 100 |
| Viscosity (20° C.), Pa.s | 27.5 | 19.5 | 20.0 | 22.5 | 10.0 | 32.5 |

| | 7 | 8 | 9 | 10 | 11 | 12 | 13 |
|---|---|---|---|---|---|---|---|
| Sident 12 SPLS | 12 | 12 | 12 | 12 | 12 | 12 | 12 |
| Sipernat 320 DS | — | 0.5 | 1.0 | 0.5 | 0.5 | 0.5 | — |
| Sorbosil BFG 51 | 0.1 | 0.1 | 0.1 | 0.1 | 0.1 | 0.1 | 0.1 |
| Sorbitol | 33.6 | 33.6 | 33.6 | 33.6 | 33.6 | 33.6 | 33.6 |
| Glycerol | 24.3 | 23.9 | 23.9 | 23.9 | 23.9 | 23.9 | 23.9 |
| Polyethylene glycol 400 | 3.5 | 3.5 | 3.5 | 3.5 | 3.5 | 3.5 | 3.5 |
| Keltrol F | 0.18 | — | — | — | — | — | — |
| Blanose 9-M-31-XF | — | 0.2 | 0.2 | 0.25 | — | 0.13 | 0.2 |
| Blanose 12-M-31-P | — | — | — | — | — | — | — |
| Luviskol K30 | — | — | — | — | — | — | — |
| Texapon K12 | 0.5 | 0.5 | 0.5 | 0.5 | 0.5 | 0.5 | 0.5 |
| Tego Betain F50 | 0.72 | 0.72 | 0.72 | 0.72 | 0.72 | 0.72 | 0.72 |
| Cremophor RH60 | — | — | — | — | — | — | 0.2 |
| Tagat S | — | — | 0.5 | — | — | — | — |
| Flavor | 0.8 | 0.8 | 1.0 | 0.8 | 0.8 | 0.8 | 0.8 |
| Na saccharin | 0.25 | 0.25 | 0.25 | 0.25 | 0.25 | 0.25 | 0.25 |
| Panthenol | — | 0.13 | 0.13 | — | — | — | — |
| Retinol palmitate | — | 0.018 | 0.018 | — | — | — | — |
| $Na_2PO_3F$ | 1.1 | 1.1 | 1.1 | 1.1 | 1.1 | 1.1 | 1.1 |
| Water | to 100 | to 100 | to 100 | to 100 | to 100 | to 100 | to 100 |
| Viscosity (20° C.), Pa.s | 26.0 | 21.25 | 22.5 | 20.0 | 37.0 | 37.0 | 18.75 |

All the Examples represent transparent gels which retain their transparency even after storage for 4 weeks at 25° C.

The following commercial products were used:

Sident® 12 SPLS:
   precipitated silica, specific surface (BET) 80 $m^2/g$, manufacturer: DEGUSSA AG Sipernat® 320 DS:
 precipitated silica, specific surface (BET) 170 m²/g, manufacturer: DEGUSSA AG Sorbosil® BFG 51:
 colored, agglomerated precipitated silica, mean particle size 310 μm (min. 90% 106–710 μm)

Keltrol® F:
 xanthan gum, manufacturer: KELCO, Brussels

Blanose® 9-M-31-XF:
 Na carboxymethyl cellulose, degree of subst. 0.8–0.95, viscosity 100–300 mPa·s (1%), manufacturer: HERCULES Blanose® 12-M-31-XP:
 Na carboxymethyl cellulose, degree of subst. 1.2, viscosity 100–300 mPa·s (1%), manufacturer: HERCULES Luviskol® K30:
 polyvinyl pyrrolidone, MW ca. 40,000, manufacturer: BASF AG Texapon® K12:
 Na lauryl sulfate (HENKEL KGaA)

Tego Betain® F50:
 N,N-dimethyl-N-cocoamidopropyl ammonium acetobetaine (ca. 36% AS), manufacturer: TEGO Cosmetics Cremophor® RH 60:
 PEG 60 Hydrogenated Castor Oil (BASF AG)

Tagat® S:
 polyoxyethylene-(20)-glycerol monostearate, manufacturer TEGO Cosmetics

What is claimed is:

1. A liquid tooth cleaning composition in the form of a transparent gel comprising:
 (a) 10 weight percent to 15 weight percent of one or more silica polishing components, based on The total weight of the composition;
 (b) 55 weight percent to 70 weight percent of humectants, based on the total weight of the composition, wherein the humectants are sorbitol, glycerol and polyethylene glycol in a weight ratio of the sorbitol to the glycerol to the polyethylene glycol of 10:(7 to 8):(0.5 to 1.5); and
 (c) 15 weight percent to 30 weight percent of water, based on the total weight of the composition.

2. The liquid tooth cleaning compositions of claim 1 wherein the water (c) and the total amount (x) of the sorbitol, glycerol and polyethylene glycol are present in a weight ratio of (c) to (x) of 1:(2 to 3).

3. The liquid tooth cleaning composition of claim 2 further comprising one or more toothpaste ingredients wherein the toothpaste ingredients comprise one or more binders, surfactants, flavorants, substances active against diseases of teeth or gums, or combinations thereof.

4. The liquid tooth cleaning composition of claim 3 wherein the toothpaste ingredients are present in an amount of 2 weight percent to 10 weight percent based on the total weight of the composition.

5. The liquid tooth cleaning composition of claim 4 further comprising from 0.1 weight percent to 1.0 weight percent of colored silica particles, based on the total weight of the composition.

6. The liquid tooth cleaning composition of claim 5 wherein the binders are present in the composition in an amount of up to 0.5 weight percent and wherein the binders are selected from the group consisting of xanthan gum, carboxymethyl cellulose, polyvinyl pyrrolidone and combinations thereof.

7. The liquid tooth cleaning composition of claim 6 wherein the composition comprises one or more of the substances active against diseases of the teeth or gums selected from the group consisting of fluorine compounds, antimicrobial agents, vitamins, mineral salts, and combinations thereof.

8. The liquid tooth cleaning composition of claim 1 further comprising 2 weight percent to 10 weight percent of additional toothpaste ingredients based on the total weight of the composition.

9. The liquid tooth cleaning composition of claim 8 wherein the additional toothpaste ingredients comprise one or more binders, surfactants, flavorants, substances active against diseases of teeth or gums, or combinations thereof.

10. The liquid tooth cleaning composition of claim 1 further comprising up to 0.5 weight percent based on the total weight of the composition of xanthan gum, carboxymethyl cellulose, polyvinyl pyrrolidone or combinations thereof.

11. The liquid tooth cleaning composition of claim 1 further comprising one or more active substances selected from the group consisting of fluorine compounds, antimicrobial agents, vitamins, mineral salts and combinations thereof.

12. The liquid tooth cleaning composition of claim 1 further comprising from 0.1 weight percent to 1.0 weight percent of colored silica particles.

* * * * *